(12) United States Patent
Levine et al.

(10) Patent No.: US 11,993,562 B2
(45) Date of Patent: May 28, 2024

(54) METHODS FOR ISOLATION AND PURIFICATION OF CANNABIDIOL (CBD) AND TERPENES FROM HEMP

(71) Applicant: RJ Lee Group, Inc., Monroeville, PA (US)

(72) Inventors: Alan M. Levine, Monroeville, PA (US); Steven J. Monaco, Venetia, PA (US); Richard J. Lee, Murrysville, PA (US); Duane M. Erickson, Natchez, MS (US)

(73) Assignee: RJ LEE GROUP, INC., Monroeville, PA (US)

( * ) Notice: Subject to any disclaimer, the term of this patent is extended or adjusted under 35 U.S.C. 154(b) by 0 days.

(21) Appl. No.: 17/657,553

(22) Filed: Mar. 31, 2022

(65) Prior Publication Data

US 2022/0324780 A1 Oct. 13, 2022

Related U.S. Application Data

(60) Provisional application No. 63/200,829, filed on Mar. 31, 2021.

(51) Int. Cl.
*C07C 37/50* (2006.01)
*C07D 311/80* (2006.01)

(52) U.S. Cl.
CPC ............ *C07C 37/50* (2013.01); *C07D 311/80* (2013.01)

(58) Field of Classification Search
CPC ....................................................... C07C 37/50
USPC ............................................................ 549/390
See application file for complete search history.

(56) References Cited

U.S. PATENT DOCUMENTS

| 2016/0228385 | A1 | 8/2016 | Sievers et al. |
| 2019/0151771 | A1 | 5/2019 | Thomas |
| 2020/0199055 | A1* | 6/2020 | Jansen ............... C07D 311/78 |

FOREIGN PATENT DOCUMENTS

WO 2016153347 A1 9/2019

OTHER PUBLICATIONS

Murayama et al., A New Centrifugal Counter-Current Chromatograph and Its Application, Journal of Chromatography A (Apr. 30, 1982), 239:643-649.

* cited by examiner

*Primary Examiner* — Taofiq A Solola
(74) *Attorney, Agent, or Firm* — Debora Plehn-Dujowich; John Desper; Eckert Seamans Cherin & Mellott, LLC (57) ABSTRACT

The invention provides a plurality of methods which may be employed as a single method or a plurality of sequential method steps in the isolation and purification of Cannabidiol from Hemp plants. It also provides methods for having a terpene-rich fraction as a byproduct of the method. Depending upon the ultimate objective, the individual method components may be used separately or combined with one or more method steps to accomplish the objectives.

21 Claims, 9 Drawing Sheets

METHODS FOR ISOLATION AND PURIFICATION OF CANNABIDIOL (CBD) AND TERPENES FROM HEMP

CROSS REFERENCE TO RELATED APPLICATIONS

This application claims priority to U.S. Provisional Patent Application No. 63/200,829, filed Mar. 31, 2021, the contents of which are incorporated herein by reference in their entirety.

FIELD OF THE INVENTION

The present invention relates to methods for isolation and purification of cannabidiol (CBD) from hemp plants. In one embodiment, a byproduct of the methods is a terpene-rich fraction. Depending upon the objectives of the user of the methods, various combinations of method steps may be employed to efficiently produce the desired result.

BACKGROUND OF THE INVENTION

The hemp plant consists primarily of an elongated stalk, leaves, seeds, flowers and roots. The processes of the present invention obtain the highest yield from the seeds, flowers, and roots, and some yield can both be obtained from the stalk and leaves. The stalk is commonly used in making paper, textiles, clothing, building materials and industrial textiles, for example.

It has been known that CBD and cannabidiolic acid (CBDA), which may be both obtained from hemp, serve many useful purposes including medical purposes such as topically applied ointments to relieve pain, use in vaping when smoking, and by oral use to minimize seizures and severe headaches. Depending upon the ultimate intended use, purity desired and potential useful byproducts, the process of obtaining the material varies.

It has been known that hemp with high levels of tetrahydrocannabinol (THC) is marijuana, which has known effects as a drug and, in many forms, is an illegal Schedule 1 drug in the United States. If, however, the amount of THC is reduced to less than about 0.3 percent by weight the compound is no longer considered as marijuana. This is reflected in the United States Code:

Federal Law: S.3042—Agriculture Improvement Act of 2018; S.3042—115th Congress (2017-2018)

"The primary federal law that allowed businesses to start marketing CBD products is the Agriculture Improvement Act of 2018. This Act legalized the farming of industrial hemp, which, as defined by the Act, contains less than 0.3% THC (THC is the chemical in cannabis that gets people high). If hemp contains more than 0.3% THC, the federal government considers it to be marijuana, which is an illegal Schedule 1 drug."

It has been known to obtain CBD from hemp by means of solvent extraction with the most common solvents being super critical carbon dioxide and ethanol (if the extraction solvent is not ethanol). Hydrocarbons, such as a butane and pentane, have also been known to be used. The extraction step is followed by a step in which the extract is dissolved in ethanol if the extraction solvent is not ethanol and chilled to around 0 degrees Farenheit or lower to precipitate waxes, sugars and other plant components. These precipitates are filtered from the CBD-containing solvent. This is followed by removal of the solvent by evaporation or distillation and then further purification of the CBD containing hemp oil by additional distillation. Removal of THC by chromatography and the preparation of isolate by crystallization can be performed on this material.

It has therefore been known for many purposes that it is desirable to purify CBD or CBDA through extraction. See, generally U.S. Published Patent Applications 2016/0228385 and 2019/0151771 (see also: WO 2016/153347).

Numerous uses of hemp in the pharmaceutical and cosmetic fields, food products, and industrial products have also been known.

There remains, therefore, a very real and substantial need for methods of purifying cannabidiol and terpenes derived from hemp.

SUMMARY

Provided herein are methods for processing hemp biomass that improve the yield of cannabinoids such as CBD and THC. In some of the methods, the related compounds CBD-A and THC-A are decarboxylated in an initial heating step, facilitating processing. Also provided herein are methods for washing hemp biomass to improve processing and decrease the amount of undesired material. Also provided are liquid-liquid extraction steps to improve the purity of the desired cannabinoid. Also provided are methods to purify the desired cannabinoid using chromatographic methods.

BRIEF DESCRIPTION OF THE DRAWINGS

The disclosure will be described in conjunction with the following drawings in which like reference numerals designate like elements and wherein.

DETAILED DESCRIPTION OF THE DISCLOSURE

Abbreviations and Definitions

"C18"=octadecyl; "DMA"=N,N-dimethylacetamide, "DMF"=N,N-dimethylformamide; DMSO=dimethyl sulfoxide; "RP"=reverse phase; WFE=wipe-film evaporator.

"About" as used herein when referring to a measurable value such as an amount, a temporal duration, and the like, is meant to encompass variations of ±5%, preferably ±1%, and still more preferably ±0.1% from the specified value, as such variations are appropriate to perform the disclosed methods.

As employed herein, the term "cannabinoid" refers to a class of compounds derived from plant in the family Cannabaceae. Members of the class include tetrahydrocannabinol (THC), cannabidiol (CBD), and cannabinol (CBN).

As employed herein, the term "CBD" refers to cannabidiol, variously named as: 1,3-benzenediol, 2-[3-methyl-6-(1-methylethenyl)-2-cyclohexen-1-yl]-5-pentyl-, (1R-trans)-; resorcinol, 2-p-mentha-1,8-dien-3-yl-5-pentyl-, (-)-(E); and (-)-trans-2-p-mentha-1,8-dien-3-yl-5-pentylresorcinol.

As employed herein, the term "THC" refers to tetrahydrocannabinol, and more specifically to (-)-trans-$\Delta^9$-tetrahydrocannabinol, also named (-)-(6aR,10aR)-6,6,9-trimethyl-3-pentyl-6a,7,8,10a-tetrahydro-6H-benzo[c]chromen-1-ol, and in the pharmaceutical industry as Dronabinol, MARINOL® and SYNDROS®.

As employed herein, the term "CBN" refers to cannabinol, named as 6,6,9-trimethyl-3-pentylbenzo[c]chromen-1-ol.

As employed herein, the term "solvent composition" refers to a composition consisting of one or more solvents. By way of example, the term embraces both pure heptane and DMSO/heptane mixtures.

As employed herein, the term "winterization" refers to the process, known in the art, of removing fats, lipids, waxes, and chlorophyll crude hemp oil by taking the oil to a sub-zero Celsius temperature, for example about −20 degrees Celsius or below, to allow the compounds above to coagulate and be removed by filtration or other means.

As employed herein, the term "hydrocarbon" refers to a compound consisting of elements chosen from carbon, hydrogen, nitrogen, and oxygen. In certain embodiments, the hydrocarbon consists of elements chosen from carbon, hydrogen, and oxygen. In certain embodiments, the hydrocarbon consists of elements chosen from carbon, and hydrogen. In certain embodiments, the hydrocarbon is aliphatic. In certain embodiments, the hydrocarbon contains one or more aromatic rings. In certain embodiments, the hydrocarbon contains one aromatic rings. In certain embodiments, the hydrocarbon has 16 or fewer carbons. In certain embodiments, the hydrocarbon has 12 or fewer carbons. In certain embodiments, the hydrocarbon has 10 or fewer carbons.

As employed herein, the term "hemp" or "industrial hemp" means one or more portions of a hemp plant. A hemp plant typically consists of elongated stalks, seeds, flowers, roots and leaves. In a preferred form as employed herein, the hemp will have less than 0.3 percent THC and therefore will not fall under the heading of marijuana.

The hemp leaves have some value in isolating CBD and have an application in use in padding in animal bedding, as well as compost and mulch. Other parts of the hemp plant serve to provide significant, meaningful uses. The roots have been used to remedy conditions such as joint pain and skin conditions, for example. The stalk can provide uses in paper products, textiles and building materials. A large number of uses for the seeds include body care products such as cosmetics, shampoos and soaps, as well as certain food products and industrial products such as coatings, solvents, paints and fuel. The buds or flowers are the primary repository for the CBD/THC.

In some embodiments of any of the compositions or methods described herein, a range is intended to comprise every integer or fraction or value within the range.

Embodiments described herein as "comprising" one or more features may also be considered as disclosure of the corresponding embodiments "consisting of" and/or "consisting essentially of" such features.

The present invention has met the hereinbefore described need by providing a series of methods which may be employed individually or selectively in combination with others within the group.

A method of processing hemp biomass in one embodiment involves heating the biomass to decarboxylate CBD-A and THC-A, to yield CBD and THC, respectively, and subsequently drying and grinding the biomass. The decarboxylation converts CBD-A to CBD, which is the active form and thereby increases the yield of CBD.

In a further stage of the method, the biomass decarboxylation step has separated output, which is condensed and yields terpenes and water.

In another embodiment, the biomass is mixed with water to remove sugars and other water-soluble components in the biomass early in the process thereby reducing the amount of material to be handled in subsequent operations. The treatment of the biomass with a basic solution, such as NaOH, serves to convert carboxylic acids, chlorophyll and metal containing enzymes into more water soluble forms, which allows their extraction into water.

A further unique component of the method, referred to as DMSO Extractive Fractionation, employs DMSO to extract the CBD from the biomass. This provides numerous benefits in terms of the separation. DMSO will readily dissolve CBD, as well as other cannabinoids, and therefore allow easy separation of the insoluble plant components. This contributes meaningfully to the yield and purity of the final CBD product.

In an optional second stage, following the first stage DMSO extraction, the DMSO extract is diluted with water, with which it is readily miscible. The mixed DMSO/water system can then be extracted with a relatively nonpolar hydrocarbon, such as heptane or another alkane. Another advantage of employing an DMSO as an extraction solvent is that, while CBD is soluble in DMSO, addition of water to the DMSO prior to the second stage liquid-liquid extraction increases the relative solubility of CBD in the hydrocarbon phase, compared to the mixed DMSO/water phase. The CBD will then preferentially partition to the hydrocarbon phase, while leaving other compounds in the DMSO/water phase. This further contributes to yield and purity.

A replacement for DMSO Extractive Fractionation, referred to as Ethanol Extraction Fractionation, employs an extraction with ethanol followed by application of a press to squeeze out CBD-containing ethanol and further processing with a wipe-film evaporator ("WFE") to yield an increased purity CBD oil.

A further embodiment replaces the ethanol extraction and pressing with a thermal reactor, referred to as Thermal Fractionation.

These three processes: DMSO Extractive Fractionation, Ethanol Extraction Fractionation, and Thermal Fractionation can be used independently or in conjunction with one another In another embodiment of the method, reverse phase chromatography is used to selectively remove THC from the purified CBD. Reverse-phase ("RP") chromatography is a technique known in the art wherein the hydroxyl moieties of silica gel, a hydrophilic material, are covalently attached to hydrophobic groups, including but not limited to octadecyl ("C18"). By means of this modification, reverse-phase chromatographic material has different applications than unmodified ("normal phase"), most notably the use of water and other hydrophilic solvents such as ethanol and acetonitrile as eluents. While CBD and THC are structurally very similar to each other and can be difficult to separate, they have different binding strengths to C18 resin, which serve to facilitate their separation.

In another embodiment of the method, the reverse phase, C18 chromatography procedure can be replaced with a centrifugal partition chromatography (CPC) to selectively remove THC from the purified CBD. While CBD and THC are structurally very similar to each other and can be difficult to separate, they have different partition affinities for specific solvents, which serves to facilitate their separation.

It is an object of the present invention to provide methods for purification of cannabidiol (CBD) and terpenes from hemp.

It is a further object of the present invention to provide methods for separation of CBD from THC.

It is yet another object of the present invention to provide a series of method embodiments, which can be used singularly or in selected combinations to improve the efficiency of the process in terms of enhanced purification without requiring a winterization step.

These and other objects of the Invention will be more fully understood from the following detailed description of the invention on reference to the illustrations appended hereto.

Provided herein is a method for processing a hemp biomass, the method comprising the steps of:
optionally adding water to the biomass; and
heating the biomass.

In some embodiments, the heating is performed at 80° C. or higher. In some embodiments, the heating is performed at 90° C. or higher. In some embodiments, the heating is performed at 100° C. or higher.

In some embodiments, the method is performed without ignition of the biomass. In some embodiments, the method is performed below about 200° C. In some embodiments, the method is performed below about 180° C. In some embodiments, the method is performed below about 160° C. In some embodiments, the method is performed below about 150° C. In some embodiments, the method is performed below about 140° C.

In some embodiments, the heating is performed at a temperature substantially from about 90° C. to about 160° C. In some embodiments, the heating is performed at a temperature substantially from about 100° C. to about 140° C. In some embodiments, the heating is performed at a temperature substantially from about 110° C. to about 130° C.

In some embodiments, the heating is performed for a period of time from about 30 min to about 240 min. In some embodiments, the heating is performed for a period of time from about 60 min to about 180 min. In some embodiments, the heating is performed for a period of time from about 90 min to about 150 min. In some embodiments, the heating is performed for a period of time from about 110 min to about 130 min.

In some embodiments, the method comprises the step of adding water to the biomass.

In some embodiments, the method further comprises the step of:
during the heating stage, separating a terpene and water vapor phase from said biomass.

In some embodiments, the method further comprises the step of:
condensing the terpene and water vapor phase.

In some embodiments, the heating reduces the initial composition of THC-A by 50% or better. In some embodiments, the heating reduces the initial composition of THC-A by 80% or better. In some embodiments, the heating reduces the initial composition of THC-A by 90% or better.

In some embodiments, the heating reduces the initial composition of CBD-A by 50% or better. In some embodiments, the heating reduces the initial composition of CBD-A by 80% or better. In some embodiments, the heating reduces the initial composition of CBD-A by 90% or better.

Also provided herein is a method for processing a hemp biomass, the method comprising the steps, performed in the following sequence, of:
(a) rinsing the hemp biomass with water;
(b) optionally, rinsing the rinsed hemp biomass with alkali;
(c) optionally, repeating the sequence of steps (a) and (b) one or more times;
(d) optionally, rinsing the hemp biomass with water; and
(e) optionally, drying the hemp biomass at elevated temperature.

In some embodiments, the method comprises the step of:
(b) rinsing the rinsed hemp biomass with alkali.

In some embodiments, the method comprises the step of:
(c) repeating the sequence of steps (a) and (b) one or more times.

In some embodiments, the method comprises the step of:
(d) rinsing the hemp biomass with water.

In some embodiments, the method comprises the step of:
(d) rinsing the hemp biomass with water until the pH of the rinse is 10 or lower.

In some embodiments, the method comprises the step of:
(d) rinsing the hemp biomass with water until the pH of the rinse is 9 or lower.

In some embodiments, the method comprises the step of:
(d) rinsing the hemp biomass with water until the pH of the rinse is 8.5 or lower.

In some embodiments, the method comprises the step of:
(e) drying the hemp biomass at elevated temperature.

In some embodiments, the alkali is aqueous base. In some embodiments, the alkali is an aqueous base chosen from LiOH, NaOH, and KOH. In some embodiments, the concentration of the aqueous base is from about 0.04 N to about 1 N. In some embodiments, the concentration of the aqueous base is from about 0.06 N to about 0.5 N. In some embodiments, the concentration of the aqueous base is from about 0.08 N to about 0.2 N.

In some embodiments, the hemp biomass is dried at a temperature above 60° C. In some embodiments, the hemp biomass is dried at a temperature above 70° C. In some embodiments, the hemp biomass is dried at a temperature above 80° C.

In some embodiments, the hemp biomass is dried at a temperature from about 80° C. to about 140° C. In some embodiments, the hemp biomass is dried at a temperature from about 90° C. to about 130° C. In some embodiments, the hemp biomass is dried at a temperature from about 100° C. to about 120° C. In some embodiments, the hemp biomass is dried at a temperature from about 105° C. to about 115° C.

Also provided herein is a method for extracting a cannabinoid-containing material from a hemp biomass, the method comprising the steps, performed in the following sequence, of:
(a) rinsing the hemp biomass with a solvent composition comprising a first solvent and, optionally, a first hydrocarbon;
(b) separating the resulting solvent composition rinse from the hemp biomass;
(c) optionally, repeating the sequence of steps (a) and (b) one or more times; and
(d) combining the solvent composition rinses.

In some embodiments, the method further comprises the successive steps of:
(e) diluting the combined solvent composition rinses with water;
(f) extracting the combined solvent composition rinses with a second hydrocarbon;
(g) optionally, repeating step (f) one or more times; and
(h) concentrating the combined second hydrocarbon extracts via evaporation, thereby obtaining the cannabinoid-containing material.

Also provided herein is a method for extracting a cannabinoid-containing material from a hemp biomass, the method comprising the steps, performed in the following sequence, of:
(a) rinsing the hemp biomass with a solvent composition comprising a first solvent and, optionally, a first hydrocarbon;
(b) separating the resulting solvent composition rinse from the hemp biomass;
(c) optionally, repeating the sequence of steps (a) and (b) one or more times;
(d) combining the solvent composition rinses;
(e) diluting the combined solvent composition rinses with water;
(f) extracting the combined solvent composition rinses with a second hydrocarbon;
(g) optionally, repeating step (f) one or more times; and
(h) concentrating the combined second hydrocarbon extracts via evaporation, thereby obtaining the cannabinoid-containing material.

In some embodiments, the first solvent is a polar solvent. In some embodiments, the first solvent is immiscible with heptane. In some embodiments, the first solvent has a dielectric constant greater than 20. In some embodiments, the first solvent has a dielectric constant greater than 30. In some embodiments, the first solvent has a dielectric constant greater than 35. In some embodiments, the first solvent is chosen from DMF, DMA, sulfolane, nitromethane, acetonitrile, and DMSO. In some embodiments, the first solvent is DMSO.

In some embodiments, the (v/v) ratio of the first solvent rinses/water at step (e) is from about 1/4 to about 4/1. In some embodiments, the (v/v) ratio of the first solvent rinses/water at step (e) is from about 1/2 to about 2/1. In some embodiments, the (v/v) ratio of the first solvent rinses/water at step (e) is from about 1/1.5 to about 1.5/1. In some embodiments, the (v/v) ratio of the first solvent rinses/water at step (e) is from about 1/1.1 to about 1.1/1.

In some embodiments, the method comprises the step of:
(e) diluting the combined first solvent rinses with a substantially equal volume of water.

In some embodiments, the method comprises the step of:
(a) rinsing the hemp biomass with a solvent composition comprising a first solvent and a first hydrocarbon.

In some embodiments, the method comprises the step of:
(c) repeating the sequence of steps (a) and (b) one or more times.

In some embodiments, the method comprises the step of:
(c) repeating the sequence of steps (a) and (b) two or more times.

In some embodiments, the (v/v) ratio of first solvent/first hydrocarbon at step (a) is from about 1/4 to about 4/1. In some embodiments, the (v/v) ratio of first solvent/first hydrocarbon at step (a) is from about 1/2 to about 2/1. In some embodiments, the (v/v) ratio of first solvent/first hydrocarbon at step (a) is from about 1/1.5 to about 1.5/1. In some embodiments, the (v/v) ratio of first solvent/first hydrocarbon at step (a) is from about 1/1.1 to about 1.1/1.

In some embodiments, the first hydrocarbon contains a single aromatic ring. In some embodiments, the first hydrocarbon contains a single benzene ring. In some embodiments, the first hydrocarbon is an aliphatic hydrocarbon. In some embodiments, the first hydrocarbon is an aliphatic hydrocarbon containing 12 or fewer carbons. In some embodiments, the first hydrocarbon is an aliphatic hydrocarbon containing 8 or fewer carbons. In some embodiments, the first hydrocarbon is chosen from pentane, hexane, and heptane. In some embodiments, the first hydrocarbon is hexane.

In some embodiments, the method comprises the step of:
(g) repeating step (f) one or more times.

In some embodiments, the method comprises the step of:
(g) repeating step (f) two or more times.

In some embodiments, the second hydrocarbon is the same as the first hydrocarbon. In some embodiments, the second hydrocarbon is an aliphatic hydrocarbon. In some embodiments, the second hydrocarbon is an aliphatic hydrocarbon containing 12 or fewer carbons. In some embodiments, the second hydrocarbon is an aliphatic hydrocarbon containing 8 or fewer carbons. In some embodiments, the second hydrocarbon is chosen from pentane, hexane, and heptane. In some embodiments, the second hydrocarbon is hexane.

Also provided herein is a method for purifying a cannabinoid-containing material, the method comprising the step of subjecting the material to chromatography.

In some embodiments, the chromatography is high-performance liquid chromatography. In some embodiments, the chromatography is reverse-phase liquid chromatography. In some embodiments, the chromatography is C18 reverse-phase liquid chromatography. In some embodiments, the eluent comprises one or more of ethanol and water.

Also provided herein is a method for purifying a cannabinoid-containing material, the method comprising the step of subjecting the material to centrifugal partition chromatography (CPC).

In some embodiments, the method for purifying a cannabinoid-containing material affords a material containing at least 70% (w/w) of CBD. In some embodiments, the method for purifying a cannabinoid-containing material affords a material containing at least 75% (w/w) of CBD. In some embodiments, the method for purifying a cannabinoid-containing material affords a material containing at least 80% (w/w) of CBD. In some embodiments, the method for purifying a cannabinoid-containing material affords a material containing at least 90% (w/w) of CBD. In some embodiments, the method for purifying a cannabinoid-containing material affords a material containing at least 95% (w/w) of CBD.

In some embodiments, the method for purifying a cannabinoid-containing material affords a material containing at most 10% (w/w) of THC. In some embodiments, the method for purifying a cannabinoid-containing material affords a material containing at most 5% (w/w) of THC. In some embodiments, the method for purifying a cannabinoid-containing material affords a material containing at most 3% (w/w) of THC. In some embodiments, the method for purifying a cannabinoid-containing material affords a material containing at most 2% (w/w) of THC.

In some embodiments, the method for purifying a cannabinoid-containing material affords a material containing at least 70% (w/w) of THC. In some embodiments, the method for purifying a cannabinoid-containing material affords a material containing at least 75% (w/w) of THC. In some embodiments, the method for purifying a cannabinoid-containing material affords a material containing at least 80% (w/w) of THC. In some embodiments, the method for purifying a cannabinoid-containing material affords a material containing at least 90% (w/w) of THC. In some embodiments, the method for purifying a cannabinoid-containing material affords a material containing at least 95% (w/w) of THC.

In some embodiments, the method for purifying a cannabinoid-containing material affords a material containing at most 10% (w/w) of CBD. In some embodiments, the method for purifying a cannabinoid-containing material affords a material containing at most 5% (w/w) of CBD. In some embodiments, the method for purifying a cannabinoid-containing material affords a material containing at most 3% (w/w) of CBD. In some embodiments, the method for purifying a cannabinoid-containing material affords a material containing at most 2% (w/w) of CBD.

Also provided is a method combining any one or more of the previous methods, provided that the methods are compatible.

FIGS. 1-5 show method portions of the invention, which can be combined and interchanged depending upon the objectives of the user. A prime objective of the present invention is to provide isolation and purification of CBD from hemp plants while offering the opportunity to produce a terpene-rich fraction as a by-product.

An important objective of the methods disclosed herein is the decarboxylation of CBD-A and THC-A. These two compounds are acid forms of CBD and THC, respectively, and both are present to some extent in hemp. Decarboxylation of CBD-A and THC-A, shown in Scheme 1, converts these two compounds to CBD and THC, respectively. Decarboxylation of these compounds at an early stage of the overall process minimizes loss of the hydrophilic acids in the later aqueous rinses steps to be described below. Decarboxylation would therefore improve the yield of the desired product, whether it be CBD or THC.

Scheme 1. Decarboxylation of CBD-A and THC-A.

Figure 1:
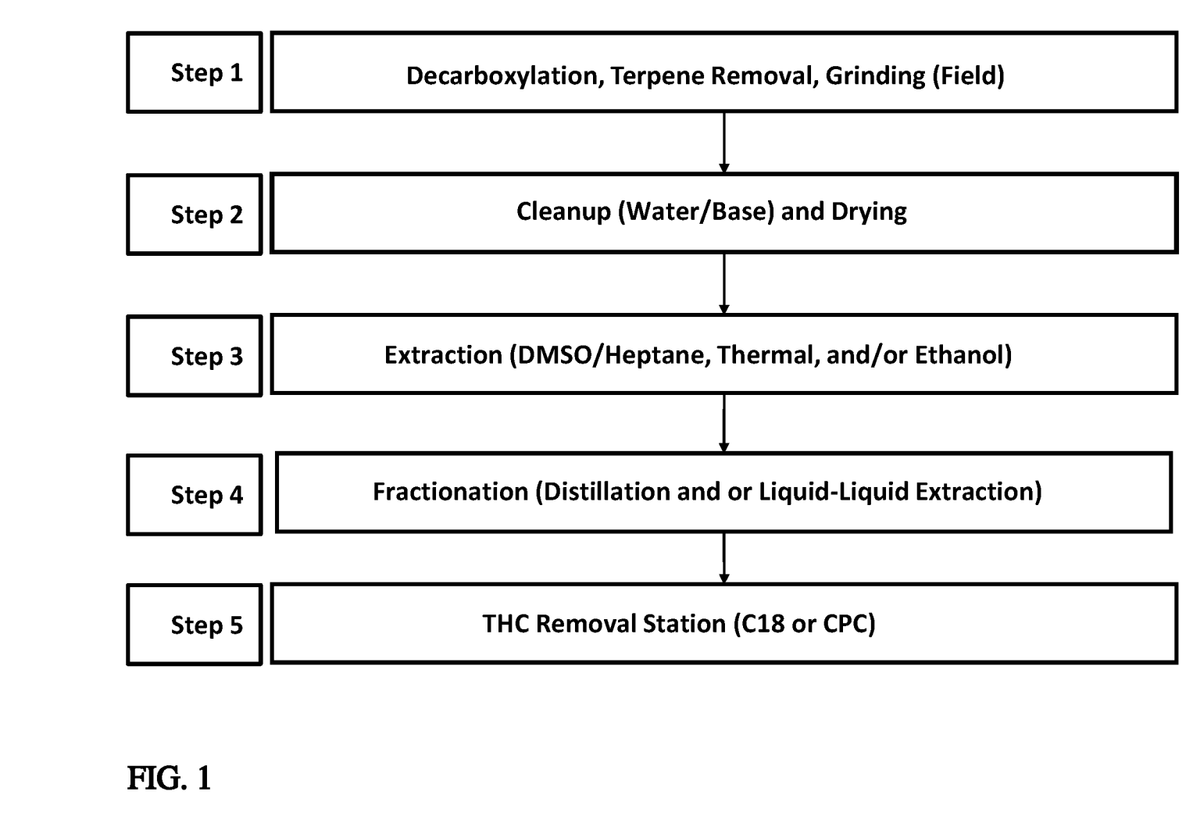
FIG. 1 is a flow diagram of a representative process. The steps can be applied individually or together.
Figure 2:
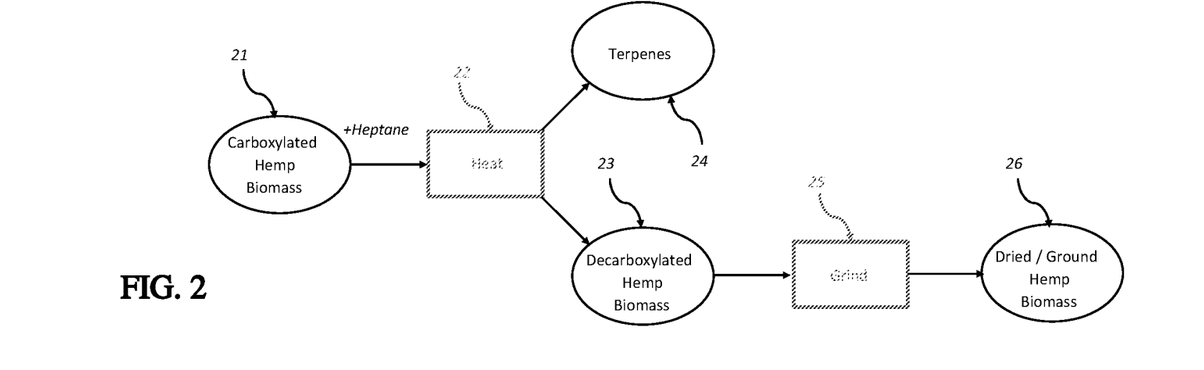
FIG. 2 is a flow diagram of a method of heating the hemp biomass to decarboxylate the acid forms of CBD and tetrahydrocannabinol (THC).

Referring to FIG. 2, the method of producing hemp biomass with a terpene-rich fraction will be considered. The hemp biomass 21 in shredded or unshredded form is heated in process 22 to at least 90° C., optionally at least 100° C., preferably from about 90° C. to about 160° C. and most preferably from about 110° C. to about 130° C. until it is dried. This process can also decarboxylate CBD-A and THC-A, which improves the yield of the process, as described above. Residual biomass 23 is carried forward. Also during the heating stage, water and various terpenes will separate in the vapor phase 24 from the plant material. Distillation of terpenes from the biomass relies on the modification of their vapor pressure due to the presence of water either from the plant material, or intentionally added to the reaction mixture.

In the next step, residual biomass 23 is ground 25, providing dried and ground biomass 26, suitable for further processing. Grinding represents a preferred way of fragmenting the biomass, but other means such as chopping and other means known to those skilled in the art may be employed. The cannabidiols CBD and THC remain in the plant material at this stage.

Figure 3:
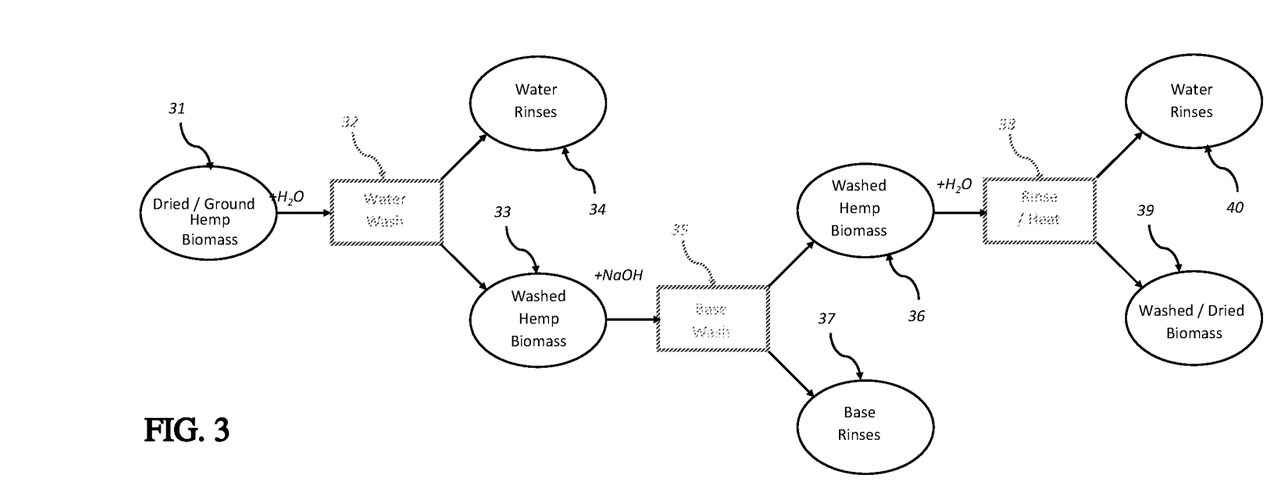
FIG. 3 is flow diagram showing a method of removing plant materials that interfere with distillation and other purification processes.

Referring to FIG. 3, the method shown removes plant materials that generally interfere with distillation and purification processes. Dried/ground hemp biomass 31 is washed in process 32 with water to afford water-washed biomass 33, from which water rinse 34 is removed. The wash step may be repeated more than once, if desired. The process may result in the removal of sugars, waxes, chlorophylls and certain other plant components. This process step can remove many of the components which are generally removed in alternative processes by a winterization step, which is not required by the present method. Avoidance of the winterization step, a costly and energy-intensive procedure, represents an important feature of this process.

The water-washed biomass 33 is then washed 35 with a basic solution such as NaOH to afford base-washed biomass 36, from which the base rinse 37 is removed. The biomass 36 is then rinsed 38 with water, multiple times if desired, to remove residual base, then pressed for thorough removal of rinse water 40 from the solid biomass. One or more of rinses 34, 37, and 40 can be processed for green disposal or recovery of other hemp components. The material can then be heated to create the dried washed biomass 39.

The base wash 35 increases the solubility of certain components yield such as chlorophyll, oils, and waxes without affecting the CBD and/or THC adversely. Decarboxylation of CBD-A and THC-A in the earlier process shown in shown in FIG. 2, circumvents loss of these two compounds, as their anionic conjugate bases, in base wash 35. The full wash procedure covers one or more water cycles, one or more base cycles and then a final water rinse to bring the material back to nearly neutral pH.

Figure 4:
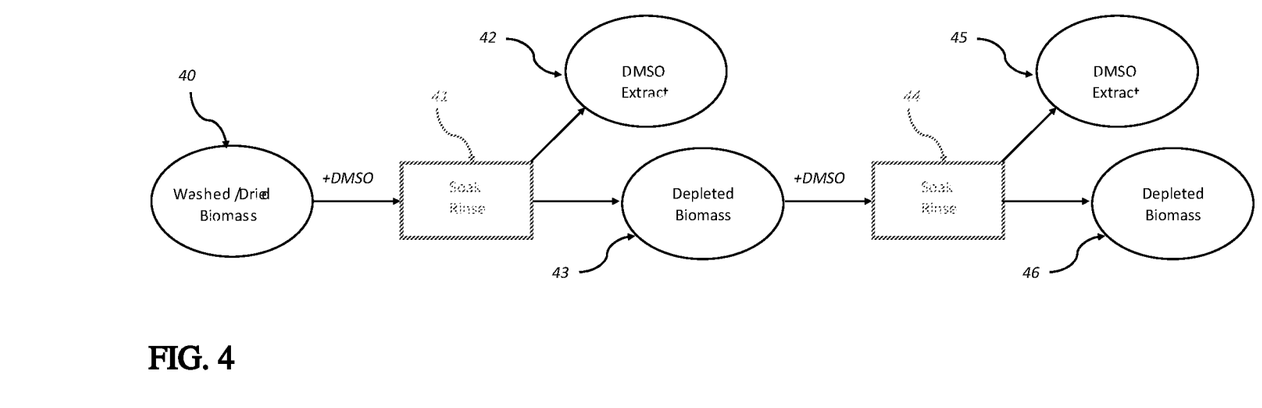
FIG. 4 is a flow diagram, which shows the decarboxylated cleaned and dried hemp in contact with DMSO to extract CBD from the biomass into the DMSO. DMSO is an organosulfur compound of the formula $(CH_3)_2SO$. It is a colorless liquid and an important polar aprotic solvent that dissolves both polar and non-polar compounds. It is miscible in a wide range of organic solvents as well as water and it has a relatively high boiling point.

In a preferred segment of the process as illustrated in FIG. 4, CBD is extracted from the biomass with DMSO. The DMSO should preferably be dry for this step. In the DMSO soak/extract portion the previously decarboxylated, cleaned and dried hemp 40 is placed in contact with DMSO one or more times to extract 41 the CBD from the biomass into the DMSO 42. It is then separated from the depleted biomass 43 (plant material) using a filter press. The process depicted includes an optional second iteration: extraction 44 of CBD from the biomass into the DMSO 45, which is separated from the depleted biomass 46. For this iterative process, DMSO extracts 42 and 45 can be combined for further processing.

Figure 5:
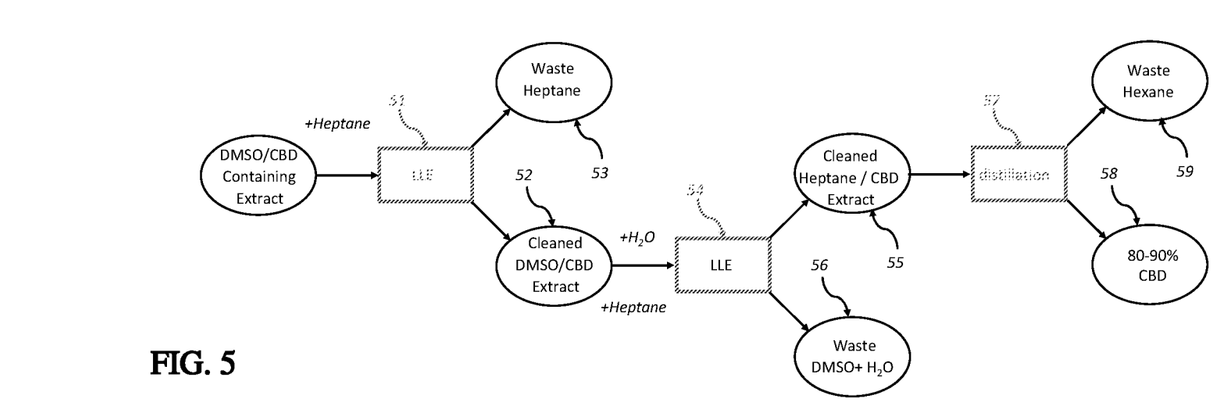
FIG. 5 shows a liquid-liquid extraction (LLE) process employing DMSO against heptane and other hydrocarbons.

Referring to FIG. 5, this shows a liquid-liquid-extraction (LLE) 51 (DMSO) against heptane or other nonpolar hydrocarbons, including alkanes from C4 through C10, as well as other hydrocarbons. The CBD-containing DMSO is first extracted by liquid-liquid extraction against heptane, which removes chlorophyll and other non-CBD plant components that were co-extracted along with the CBD, which in contrast is retained in DMSO phase 52. The waste heptane is removed as 53.

The DMSO phase 52 is then mixed with water and 1:1 to 1:2 (DMSO: $H_2O$) or greater, and a second liquid-liquid extraction 54 is performed on the diluted DMSO+$H_2O$ solution. At this point, the CBD transfers to the heptane phase, affording a CBD rich heptane solution 55, which is nominally 80 to 90 percent CBD. The DMSO+$H_2O$ phase 56 is separated, and the DMSO is also recoverable for use in future extractions. Distillation is then provided at 57 to remove volatile heptane 58 and provide a CBD-rich residue 59. The heptane from 53 and 58 can be recovered for reuse.

Figure 6:
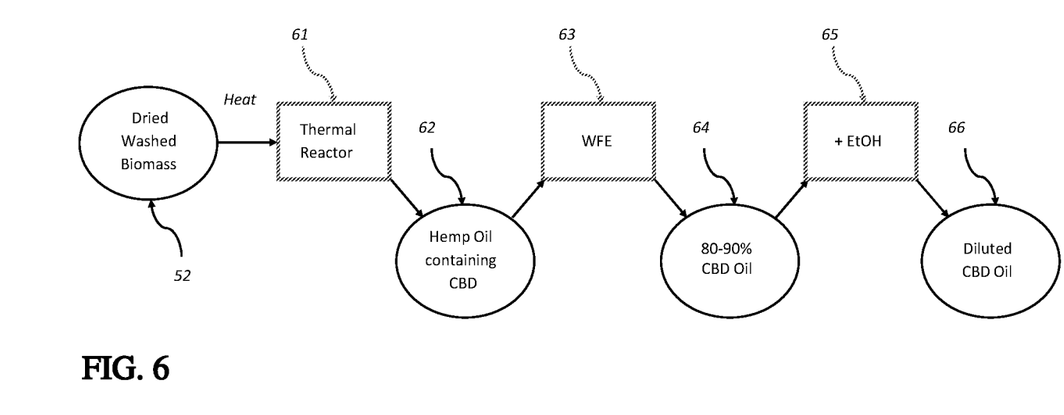
FIG. 6 is a flow diagram, which shows the a thermal distillation process that can replace the DMSO/Heptane process.

Referring to FIG. 6, this details the Thermal Fractionation alternative method for processing the washed hemp biomass. In a similar fashion to ethanol extraction, CBD oil is separated from biomass 52 using thermal reactor 61 to evaporate the oil from the biomass. The reactor consists of a heated tube and is transported through the tube using an auger. The gas is pumped under a minimal vacuum through a condenser where it is cooled to room temperature and collected by gravity into a collection vessel. The condensed oil is further separated using a wipe-film-evaporator 63 to remove heavier components from the CBD oil. At this stage the CBD/THC-containing oil 64 should be from about 80% to about 90% pure. To the oil is then added EtOH in process 65 to provide diluted CBD oil 66.

Figure 7:
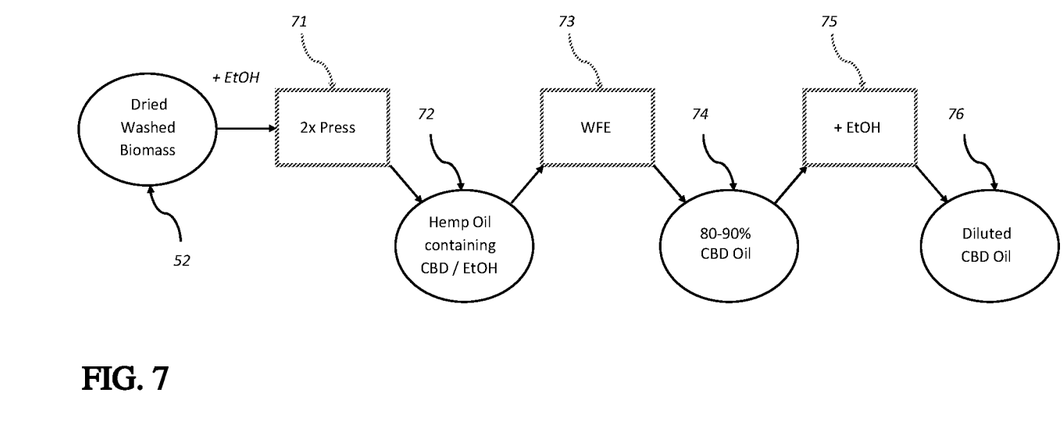
FIG. 7 is a flow diagram, which shows an ethanol extraction process using a press to separate ethanol extracted CBD Oil.

Referring to FIG. 7, this details the Ethanol Extraction alternative method for processing the washed hemp biomass. To the biomass 52 is added EtOH, following by application of press to separate hemp oil 72 from the solids. The oil is processed with a wipe-film evaporator ("WFE") 73, providing CBD oil 74, which should be from about 80% to about 90% pure. To the oil is then added EtOH in process 75 to provide diluted CBD oil 76.

In one embodiment of this invention CBD oil is extracted from washed cannabinoid-oil-containing biomass using ethanol. The extracted oil is separated from the solids using a press once or twice. The ethanol containing extract is them separated using a wipe-film-evaporator to remove the ethanol from the CBD oil and heavier components. At this stage the CBD/THC-containing oil should be from about 80% to about 90% pure.

Figure 8:
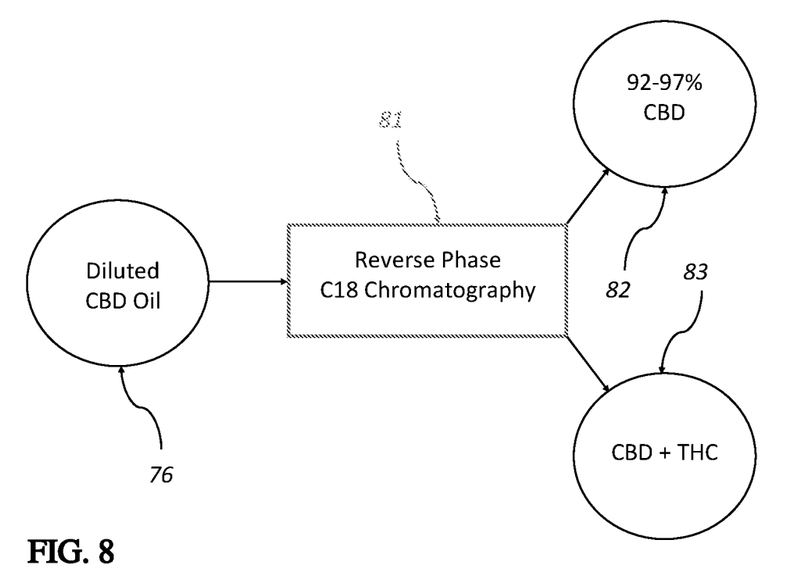
FIG. 8 shows a schematic drawing of a process for removing THC by reverse phase chromatography (RPC).

Referring to FIG. 8, this shows removal of the residual THC from the CBD using reverse phase chromatography. An efficient way of doing this is by C18 reverse phase chromatographic procedure 68. The CBD rich oil obtained from the DMSO/heptane liquid-liquid extraction is charged onto a reverse phase. Thereafter the hemp oil/CBD is charged onto C18 chromatographic column 76. The CBD and THC selectively absorb onto the C18 column and then are extracted and chromatographically separated with a solvent such as ethanol, for example. The THC is then separated with the CBD 80 employing and extracted using ethanol. This generates a 92 to 97 percent CBD 82 and a THC-rich fraction 83.

Figure 9:
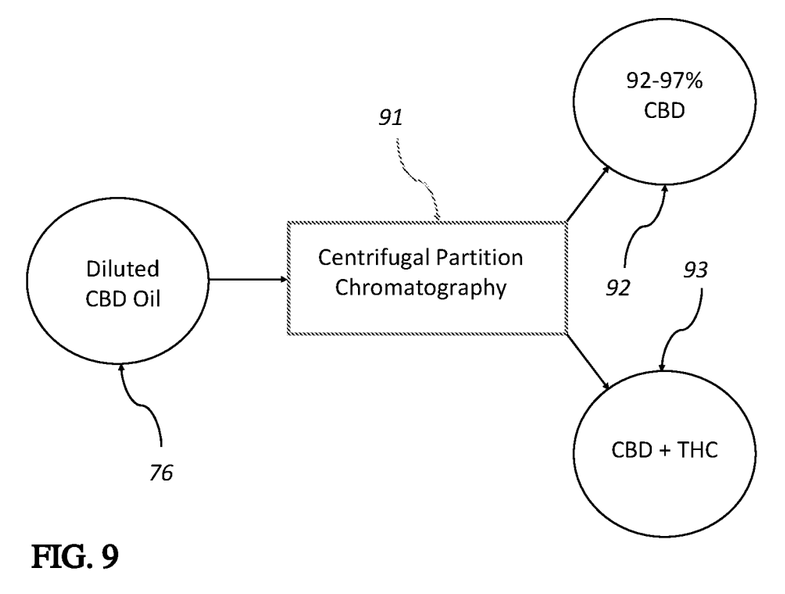
FIG. 9 shows a schematic drawing of a process for removing THC by centrifugal partition chromatography (CPC). The RPC and CPC procedures can be exchanged for each other as a final stage cleanup in the current process.

Referring to FIG. 9, this shows the centrifugal partition chromatography process for separating CBD from THC. The structures of CBD and THC are similar, and these two compounds are difficult to separate, particularly on a kg scale. These compounds can be enriched through partitioning by liquid-liquid extraction, however, many cycles are required for effective separation. A technique known a centrifugal partition chromatography (CPC) can be used for this on a large scale. This is a known technique for performing liquid-liquid extractions on a continuous basis. The technology is based on counter-current distribution, developed on a laboratory scale in the late 1930's and commercialized in the early 1940's by a corporation named Hecker. More recently the technique has been scaled to commercial size by Gilson and several other companies (Murayama, W. et al., *J. Chromatogr.* 1982, 239, 643-649). Hemp oil 76, dissolved in ethanol or another suitable solvent is fed to the instrumentation 91. instrumentation will output CBD-rich and THC rich fractions 92 and 93, respectively.

If desired, a CBD isolate of higher purity can be obtained from the product of the chromatography step through crystallization. The various steps described in respective FIGS. 1-5 can be varied as to individual step or sequence and number of steps employed depending on the objectives of the user and still provide an effective separation and purification of CBD from hemp plant material (biomass).

Several examples of variations will be considered. It will be appreciated that the examples provided and disclosed regarding FIGS. 1-5 may be used individually or in various combinations depending upon objectives of the person employing the process. Also, depending upon the user's objectives, portions each of the process steps illustrated in FIGS. 1-5 may be eliminated. For example, referring again to FIG. 2, the initial drying step as applied to the hemp biomass 21 results in lighter terpene species and decarboxylated biomass. If it is desired, however, to produce a product containing CBD-A and/or THC-A the drying step can be eliminated. With reference to FIG. 3, the biomass wash 32, base wash 35, and rinse 38 may be eliminated or all may be employed together. Optionally, the initial wash 32 can be completed alone or the base wash 35 and final rinse 38 can be completed without the initial wash, which creates four possible routes. These may be (1) no washes, (2) wash-base-wash and rinse, (3) wash, or (4) base wash-rinse.

It will further be appreciated that alternative solvents to heptane may be employed. Preferred solvents are relatively nonpolar, so as not to mix with the DMSO phase, and are relatively nonvolatile, so as to afford facile removal via evaporation or distillation. Suitable solvents include low molecular weight aliphatic and aromatic compounds.

It will further be appreciated that alternative solvents to DMSO may be employed. Preferred solvents are relatively polar, so as not to mix with the heptane phase, and are fully miscible with water. Suitable solvents include acetonitrile, sulfolane, N,N-dimethylformamide, N,N-dimethylacetamide, pyrrolidinone, trimethylene urea, HMPA, and DMPU.

By way of further example with reference to the hereinbefore discussed FIG. 7 liquid-liquid extraction, the DMSO extraction and liquid-to-liquid partition between DMSO/water and heptane (or other hydrocarbon) may be accomplished in various ways. Variations of the process unit shown in FIG. 7 can be employed: the biomass can be contacted with DMSO and the heptane simultaneously in a three-phase solid-liquid-liquid system. The DMSO and heptane will both extract material from the biomass. The CBD preferentially partitions to the DMSO while much of the chlorophyll and other extractants partition to the heptane. The solids and the liquid phases are then filtered/separated resulting in a CBD-Containing DMSO phase ready for water addition and a second liquid-liquid extraction with heptane.

Heptane can be used to extract CBD from biomass first without employing DMSO. The biomass can be removed from the heptane by filtration and then this heptane is contacted with DMSO in a liquid-liquid-extraction. The CBD preferentially transfers to the DMSO and then this CBD-Containing DMSO phase is ready for water addition and the second-liquid-liquid extraction with heptane. After the CBD-containing DMSO extract is separated from the biomass, the first-liquid-liquid extraction, which involves DMSO/heptane with no water, can be eliminated and instead the water may be added to DMSO and the liquid-liquid extraction with heptane completed. In this case, many of the compounds normally removed in the first-liquid-liquid extraction will transfer to the heptane phase along with CBD resulting a less pure product.

Another variation considering the FIG. 8 embodiment is that the THC-removal and/or CBD isolate crystallization are not required if CBD product after the liquid extractions is of sufficient purity for the intended application.

EXAMPLES

Example 1: Biomass Pretreatment

Initial drying/decarboxylation Fresh biomass was ground and sieved to 20 mesh. In a tray was heated 200 g of ground and sieved biomass in an oven at 110° C. for 2 hr. After cooling the weight of the recovered material was 184 g recovered, representing 8.0% loss.

Wash/base treatment In a beaker were combined 100 g dried/decarboxylated biomass with 750 ml water. The mixture was stirred until the biomass was fully wetted. The biomass was rinsed with water in a 100 mesh sieve until little silt remained. The wet biomass was returned to the beaker and mixed with 500 ml of 0.12 N NaOH solution. The wet biomass was then rinsed with water in a 100 mesh sieve until the pH of the rinse water was approximately 8. The biomass was then heated in an oven at 110° C. until fully dried. After cooling, the weight of the material was 63 g, representing 37% loss.

Example 2: Liquid-Liquid Extraction of Pretreated Biomass

The dried and base-treated biomass from Example 1 (20 g) was mixed with a 1:1 mixture of DMSO and heptane (100 g each) and then the solids sieved from the liquid. The solids were then extracted two more times with DMSO:heptane (50g:50g then 25g:25g). The combined liquids were then partitioned in a separatory funnel. The heptane fraction was evaporated and the oil remaining was analyzed via GC-MS.

Figure 10:
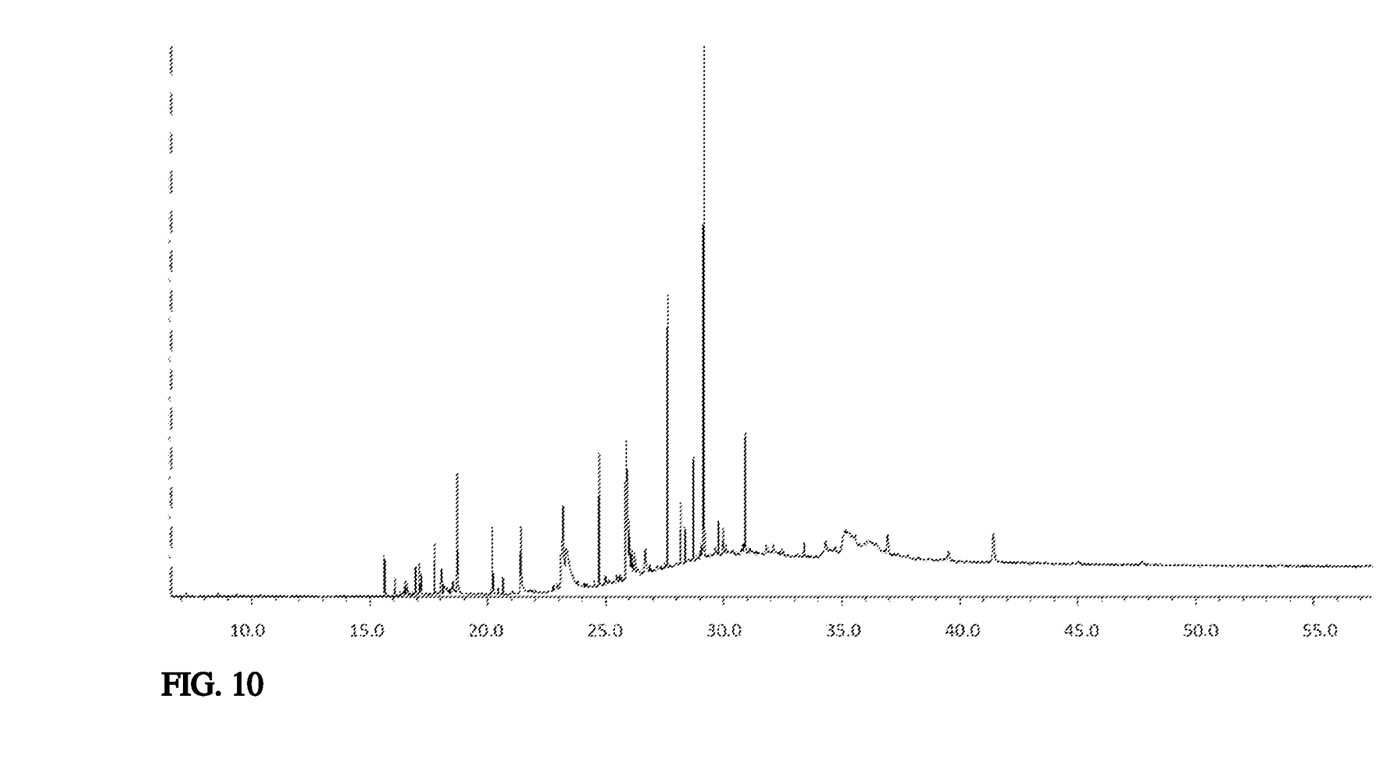
FIG. 10 shows GC/MS analysis of the first combined heptane extracts from pretreated biomass.

Shown in FIG. 10 is a GC/MS analysis of the combined heptane extracts. Table 1 reports the components in this extract. In all of Tables 1-4, assignments of the identities for the various compounds is made from a best match from spectral data.

TABLE 1

GC-MS analysis of first combined heptane extracts from pretreated biomass

| RT (min) | Area Pct | Library/ID | CAS |
| --- | --- | --- | --- |
| 15.623 | 1.2402 | Caryophyllene | 87-44-5 |
| 16.9541 | 1.1077 | α-Humulene | 6753-98-6 |
| 17.0982 | 1.041 | Naphthalene, 1,2,3,5,6,7,8,8a-octahydro-1,8a-dimethyl-7-(1-methylethenyl)-, [1R-(1α,7β,8aα)]- | 4630-07-3 |
| 17.1915 | 0.9008 | Naphthalene, 1,2,3,4,4a,5,6,8a-octahydro-4a,8-dimethyl-2-(1-methylethylidene)-, (4aR-trans)- | 6813-21-4 |
| 17.7426 | 1.6535 | Caryophyllene oxide | 1139-30-6 |
| 18.7006 | 3.6976 | α-Bisabolol | 72691-24-8 |
| 20.1928 | 1.7655 | Neophytadiene | 504-96-1 |
| 21.3967 | 3.4975 | n-Hexadecanoic acid | 57-10-3 |
| 23.1856 | 8.8572 | 9,12,15-Octadecatrienoic acid, (Z,Z,Z)- | 463-40-1 |
| 23.3212 | 9.3262 | Phytol | 150-86-7 |
| 25.8732 | 11.084 | CBD | 13956-29-1 |
| 26.1106 | 0.6696 | Eicosane | 112-95-8 |
| 26.6871 | 2.0327 | THC | 1972-08-3 |
| 27.6197 | 7.5976 | Heptacosane | 593-49-7 |
| 28.1708 | 1.7812 | 3-Methylheneicosane | 6418-47-9 |
| 28.3658 | 1.1558 | Octadecane | 593-45-3 |
| 28.7134 | 4.011 | 2,6,10,14,18,22-Tetracosahexaene, 2,6,10,15,19,23-hexamethyl-, (all-E)- | 111-02-4 |
| 29.1628 | 19.8465 | Tetracosane | 646-31-1 |
| 29.9852 | 1.0172 | Octadecane, 1-iodo- | 629-93-6 |
| 30.9093 | 5.0207 | Eicosane | 112-95-8 |

To the combined DMSO phases (~175 g) was added 175 g of water+100 g heptane. The combined phases were mixed and allowed to settle in a separatory funnel. The layers were separated, and the DMSO/water phase was extracted two more times, with 50 g and 25 g of heptane, respectively. The combined heptane fraction was evaporated and the oil remaining was analyzed by GC-MS.

Figure 11:
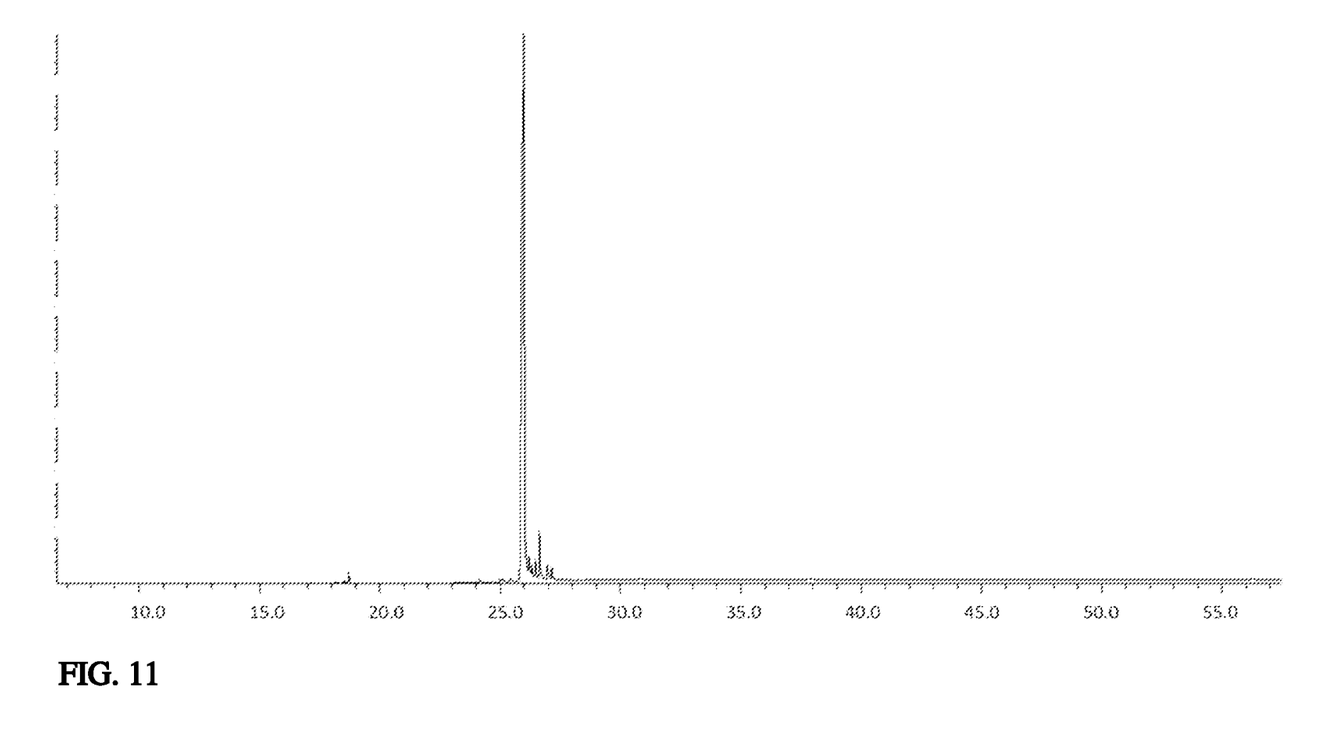
FIG. 11 shows GC/MS analysis of the second combined heptane extracts from pretreated biomass.

Shown in FIG. 11 is a GC/MS analysis of the second combined heptane extract. Table 2 reports the components in this extract.

TABLE 2

GC-MS analysis of second combined heptane extracts from pretreated biomass

| RT (min) | Area Pct | Library/ID | CAS |
|---|---|---|---|
| 18.7090 | 0.6279 | α-Bisabolol | 72691-24-8 |
| 25.4407 | 0.3162 | 1H-4-Oxabenzo(f)cyclobut(cd)inden-8-ol, 1a-α,2,3,3a,8b-α,8c-α-hexahydro-1,1,3a-trimethyl-6-pentyl- | 21366-63-2 |
| 25.9918 | 87.6669 | CBD | 13956-29-1 |
| 26.3055 | 1.5500 | THC | 1972-08-3 |
| 26.4751 | 1.7266 | β-Cannabielsoin | 52025-76-0 |
| 26.6362 | 3.4795 | THC | 1972-08-3 |
| 26.9583 | 1.5266 | 1,3-Benzenediol, 2-(3,7-dimethyl-2,6-octadienyl)-5-pentyl- | 2808-33-5 |
| 27.1533 | 0.9195 | Cannabinol | 521-35-7 |

Example 3: Liquid-Liquid Extraction of Non-Pretreated Biomass

To show the effect of the biomass pre-treatment, the above was repeated using fresh (undried, not washed or base-treated) biomass. The procedure was modified slightly to compensate for the formation of waxy precipitates in the DMSO/heptane mixture. Note that these are compounds that the pretreatment step is removing by design.

Figure 12:
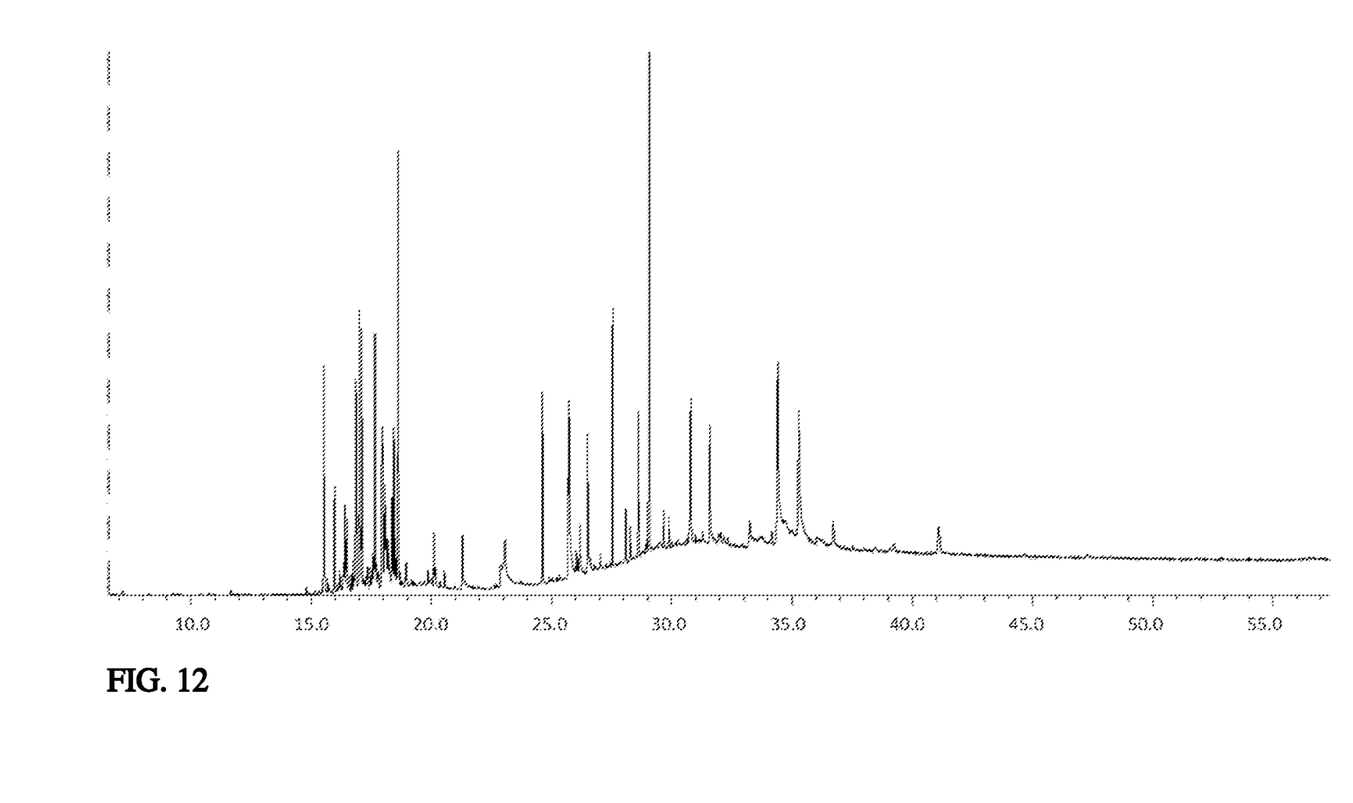
FIG. 12 shows GC/MS analysis of the first combined heptane extracts from non-pretreated biomass.

Shown in FIG. 12 is a GC/MS analysis of the corresponding first combined heptane extracts of the non-pretreated biomass. Table 3 reports the components in this extract.

TABLE 3

GC-MS analysis of first combined heptane extracts from non-pretreated biomass

| RT (min) | Area Pct | Library/ID | CAS |
|---|---|---|---|
| 15.5298 | 2.8534 | Caryophyllene | 87-44-5 |
| 15.6908 | 0.1528 | 1,6,10-Dodecatriene, 7,11-dimethyl-3-methylene-, (E)- | 18794-84-8 |
| 15.9791 | 1.193 | α-Caryophyllene | 6753-98-6 |
| 16.1826 | 0.3019 | Naphthalene, 1,2,3,4,4a,5,6,8a-octahydro-7-methyl-4-methylene-1-(1-methylethyl)-, (1α,4aα,8aα)- | 30021-74-0 |
| 16.2335 | 0.2186 | Naphthalene, 1,2,4a,5,6,8a-hexahydro-4,7-dimethyl-1-(1-methylethyl)-, (1α,4aα,8aα)- | 31983-22-9 |
| 16.3437 | 0.4715 | 2-Isopropenyl-4a,8-dimethyl-1,2,3,4,4a,5,6,7-octahydronaphthalene | 1000192-43-5 |
| 16.4115 | 1.1633 | 1H-Cycloprop[e]azulene, decahydro-1,1,7-trimethyl-4-methylene-, [1αR-(1aα,4aβ,7α,7aβ,7bα)]- | 25246-27-9 |
| 16.5048 | 1.5117 | Naphthalene, decahydro-4a-methyl-1-methylene-7-(1-methylethylidene)-, (4aR-trans)- | 515-17-3 |
| 16.6828 | 0.2331 | 1,6-Cyclodecadiene, 1-methyl-5-methylene-8-(1-methylethyl)-, [s-(E,E)]- | 23986-74-5 |
| 16.7506 | 0.3744 | Naphthalene, 1,2,3,5,6,8a-hexahydro-4,7-dimethyl-1-(1-methylethyl)-, (1S-cis)- | 483-76-1 |
| 17.0135 | 3.8962 | β-Panasinsene | 1000159-39-0 |
| 17.1067 | 3.545 | Naphthalene, 1,2,3,4,4a,5,6,8a-octahydro-4a,8-dimethyl-2-(1-methylethylidene)-, (4aR-trans)- | 6813-21-4 |
| 17.6578 | 3.9629 | Caryophyllene oxide | 1139-30-6 |
| 18.0393 | 0.9472 | 10s,11s-Himachala-3(12),4-diene | 60909-28-6 |
| 18.4463 | 2.1414 | 2-Methoxy-8-methyl-1,4-naphthalindione | 37867-02-0 |
| 18.6243 | 6.0599 | α-Bisabolol | 515-69-5 |
| 18.955 | 0.6738 | 1-Naphthalenol, decahydro-1,4a-dimethyl-7-(1-methylethylidene)-, [1R-(1α,4aβ,8aα)]- | 473-04-1 |
| 20.108 | 0.7249 | Neophytadiene | 504-96-1 |
| 21.3119 | 1.1647 | n-Hexadecanoic acid | 057-10-3 |
| 23.0754 | 2.4088 | 9,12,15-Octadecatrienoic acid, (Z,Z,Z)- | 463-40-1 |
| 25.7291 | 5.2294 | CBD | 13956-29-1 |
| 26.0258 | 0.3472 | Eicosane | 112-95-8 |
| 26.1784 | 0.9331 | THC | 1972-08-3 |
| 26.5091 | 2.4732 | THC | 1972-08-3 |
| 27.0432 | 0.2761 | Cannabinol | 521-35-7 |
| 27.535 | 2.6686 | Heptacosane | 593-49-7 |
| 28.2726 | 0.5222 | Eicosane | 112-95-8 |
| 28.6202 | 2.0929 | 2,6,10,14,18,22-Tetracosahexaene, 2,6,10,15,19,23-hexamethyl-, (all-E)- | 111-02-4 |
| 29.0695 | 7.338 | Nonacosane | 630-03-5 |
| 29.8749 | 0.4497 | 20ξ-Lanosta-7,9(11)-diene-3β,18,20-triol | 025116-58-9 |
| 30.7991 | 2.8974 | Octacosane | 630-02-4 |
| 31.5876 | 2.3105 | Vitamin E | 059-02-9 |
| 34.4023 | 6.5677 | Stigmast-7-en-3-ol, (3β,5α,24S)- | 018525-35-4 |
| 35.2841 | 5.7471 | β-Amyrin | 559-70-6 |
| 36.7169 | 0.883 | Urs-12-en-24-oic acid, 3-oxo-, methyl ester, (+)- | 020475-86-9 |

Figure 13:
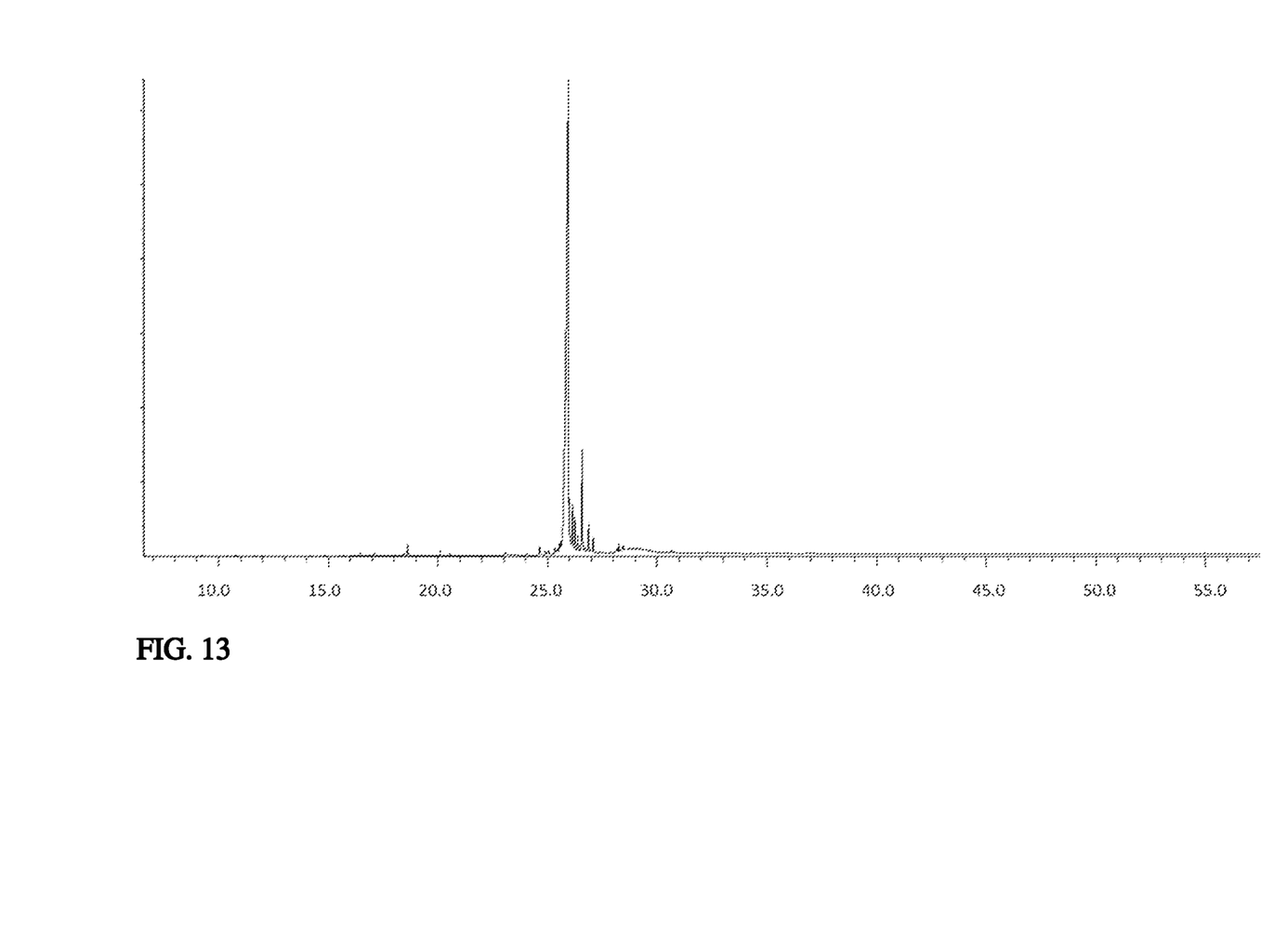
FIG. 13 shows GC/MS analysis of the second combined heptane extracts from non-pretreated biomass.

Shown in FIG. 13 is a GC/MS analysis of the corresponding second combined heptane extracts of the non-pretreated biomass. Table 4 reports the components in this extract.

TABLE 4

GC-MS analysis of second combined heptane extracts from non-pretreated biomass

| RT (min) | Area Pct | Library/ID | CAS |
|---|---|---|---|
| 16.3776 | 0.0756 | Naphthalene, 1,2,4a,5,8,8a-hexahydro-4,7-dimethyl-1-(1-methylethyl)-, [1S-(1α,4αβ,8aα)]- | 523-47-7 |
| 16.4708 | 0.1057 | Cyclohexene, 1-methyl-4-(5-methyl-1-methylene-4-hexenyl)-, (S)- | 495-61-4 |
| 17.0982 | 0.1727 | Neoisolongifolene, 8,9-dehydro- | 067517-14-0 |
| 18.0393 | 0.0679 | Selina-6-en-4-ol | 1000140-23-2 |
| 18.4463 | 0.1429 | 2-Methoxy-8-methyl-1,4-naphthalindione | 037867-02-0 |
| 18.6158 | 0.5484 | α-Bisabolol | 072691-24-8 |
| 18.9635 | 0.0524 | 1-Naphthalenol, decahydro-1,4a-dimethyl-7-(1-methylethylidene)-, [1R-(1α,4aβ,8aα)]- | 473-04-1 |
| 20.108 | 0.1733 | Neophytadiene | 504-96-1 |
| 20.5574 | 0.0699 | Neophytadiene | 504-96-1 |
| 23.1008 | 0.3786 | 9,12,15-Octadecatrienoic acid, (Z,Z,Z)- | 463-40-1 |
| 24.94491 | 0.1701 | 3-Bromo-5-ethoxy-4-hydroxybenzaldehyde | 3111-37-3 |
| 25.0508 | 0.3296 | Resorcinol, 2-p-mentha-1,8-dien-3-yl-5-pentyl-, (−)-(E)- | 521-37-9 |
| 25.3391 | 0.7869 | 2H-1-Benzopyran-5-ol, 2-methyl-2-(4-methyl-3-pentenyl)-7-pentyl- | 020675-51-8 |
| 25.4747 | 0.3771 | Resorcinol, 2-p-mentha-1,8-dien-3-yl-5-pentyl-, (−)-(E)- | 521-37-9 |
| 25.5341 | 0.5883 | Resorcinol, 2-p-mentha-1,8-dien-3-yl-5-pentyl-, (−)-(E)- | 521-37-9 |
| 25.6019 | 0.9059 | 1,3-Benzenediol, 2-[3-methyl-6-(1-methylethenyl)-2-cyclohexen-1-yl]-5-pentyl-, (1R-trans)- | 521-37-9 |
| 25.9411 | 74.4188 | CBD | 13956-29-1 |
| 26.2378 | 2.3265 | THC | 1972-08-3 |
| 26.3819 | 1.463 | β-Cannabielsoin | 52025-76-0 |
| 26.5769 | 6.3338 | THC | 1972-08-3 |
| 26.6871 | 0.3179 | 8-Chloro-1,2,3,4-tetrahydro-1-methyl-6-phenyl-1,5-benzodiazocin-2-one | 017954-18-6 |
| 26.7295 | 0.3223 | 1,3-Benzenediol, 5-pentyl-2-(4,6,6-trimethylbicyclo[3.1.1]hept-3-en-2-yl)-, (1α,2α,5α)- | 016814-28-1 |
| 26.8821 | 1.5416 | 1,3-Benzenediol, 2-(3,7-dimethyl-2,6-octadienyl)-5-pentyl- | 2808-33-5 |
| 27.0687 | 0.8026 | Cannabinol | 521-35-7 |
| 28.1623 | 0.3871 | 2-Hydroxy-3-methyl-4,6-dimethoxymethyl-benzophenone | 074627-90-0 |
| 28.3489 | 0.085 | 4-Pregnen-21-ol-3,20-dione glucoside | 1000255-23-6 |
| 28.4337 | 0.7014 | Androstan-3-one, (aminocarbonyl)hydrazone, (5α)- | 054725-03-0 |
| 30.6634 | 0.1378 | 1,3-Benzenediol, 2-(3,7-dimethyl-2,6-octadienyl)-5-pentyl- | 2808-33-5 |

All publications and patents referred to herein are incorporated by reference. Whereas particular embodiments of this invention have been described herein for purposes of illustration, it will be evident to those skilled in the art that numerous variations of the details of the present invention may be made without departing from the invention as defined in the appended claims.

What is claimed is:

1. A method of processing hemp and increasing the yield of CBD, the method comprising the steps of:
   heating the hemp to a temperature from about 90° C. to about 160° C. until it is dried to decarboxylate acid species comprising CBD-A and/or THC-A within the hemp to increase the yield of CBD,
   drying and fragmenting said hemp;
   subjecting said dried and fragmented hemp to water washing to remove materials that interfere with distillation and purification; and
   extracting CBD by placing said hemp in contact with DMSO;
   wherein the method is performed without ignition of the hemp.

2. The method of claim 1, further comprising the steps of:
   during the heating stage, separating a terpene and water vapor phase from said hemp; and
   condensing the terpene and water vapor phase.

3. The method of claim 2 wherein the heating is effected at 100° C. or above.

4. The method of claim 1, further comprising the step of:
   separating said CBD from said DMSO by employing a liquid-to-liquid extraction of DMSO against an alkane to effect extraction of said CBD from DMSO.

5. The method of claim 1, further comprising the step of:
   employing a C18 chromatographic separation system to remove THC.

6. The method of claim 1, further comprising the steps of:
separating THC from CBD; and
employing reverse phase chromatography to separate THC from CBD.

7. A method for processing hemp to improve extraction efficiency, the method comprising the steps, performed in the following sequence, of:
(a) rinsing the hemp with water;
(b) rinsing the rinsed hemp with alkali, wherein the alkali is an aqueous base chosen from LiOH, NaOH, and KOH;
(c) optionally, repeating the sequence of steps (a) and (b) one or more times;
(d) optionally, rinsing the hemp with water; and
(e) optionally, drying the hemp at elevated temperature.

8. The method of claim 7, wherein the concentration of the aqueous base is from about 0.08 N to about 0.2 N.

9. The method of claim 8, comprising the step of:
(d) rinsing the hemp with water.

10. The method of claim 9, comprising the step of:
(d) rinsing the hemp with water until the pH of the rinse is 8.5 or lower.

11. The method of claim 10, comprising the step of:
(e) drying the hemp at elevated temperature.

12. A method for extracting a cannabinoid-containing material from hemp for improved yield and purity, the method comprising the steps, performed in the following sequence, of:
(a) rinsing the hemp with a solvent composition comprising a first solvent chosen from DMF, DMA, sulfolane, nitromethane, acetonitrile, and DMSO, and, optionally, a first hydrocarbon;
(b) separating the resulting solvent composition rinse from the hemp;
(c) optionally, repeating the sequence of steps (a) and (b) one or more times;
(d) combining the solvent composition rinses;
(e) diluting the combined solvent composition rinses with water;
(f) extracting the combined solvent composition rinses with a second hydrocarbon;
(g) optionally, repeating step (e) one or more times; and
(h) concentrating the combined second hydrocarbon extracts via evaporation, thereby obtaining the cannabinoid-containing material.

13. The method of claim 12, wherein the second hydrocarbon is the same as the first hydrocarbon.

14. The method of claim 13, wherein the first hydrocarbon is an aliphatic hydrocarbon.

15. The method of claim 12, wherein the first solvent is DMSO.

16. The method of claim 15, wherein the (v/v) ratio of the first solvent rinses/water at step (e) is from about 1/2 to about 2/1.

17. The method of claim 15, wherein the (v/v) ratio of first solvent/first hydrocarbon at step (a) is from about 1/2 to about 2/1.

18. The method of claim 12, further comprising the step of purifying the cannabinoid-containing material.

19. The method of claim 18, wherein the purification is accomplished with reverse-phase chromatography.

20. The method of claim 18, wherein the purification is accomplished with centrifugal partition chromatography (CPC).

21. The method of claim 1, with the proviso that the method does not include a winterization step.

* * * * *